(12) United States Patent
Ku et al.

(10) Patent No.: US 8,071,142 B2
(45) Date of Patent: Dec. 6, 2011

(54) **ANTI-BACTERIAL USE OF EXTRACT FROM *MORUS AUSTRALIS* POIR. AND COMPOUND KUWANON H**

(75) Inventors: Yuan-Ling Ku, Taipei (TW); Shih-Tsun Liang, Taipei (TW); Yu-Hsuan Lin, Taipei (TW); Liang-Hua Chen, Taipei (TW); Ying-Yu Kuo, Taipei (TW); Feng-Nien Ko, Taipei (TW)

(73) Assignee: Medical and Pharmaceutical Industry Technology and Development Center, Taipei (TW)

( * ) Notice: Subject to any disclaimer, the term of this patent is extended or adjusted under 35 U.S.C. 154(b) by 0 days.

(21) Appl. No.: 12/345,254

(22) Filed: Dec. 29, 2008

(65) Prior Publication Data

US 2010/0166898 A1      Jul. 1, 2010

(51) Int. Cl.
*A61K 36/00* (2006.01)
*A61K 36/605* (2006.01)
(52) U.S. Cl. .................................. 424/775; 424/725
(58) Field of Classification Search .................. None
See application file for complete search history.

(56) References Cited

FOREIGN PATENT DOCUMENTS

JP          10007555 A  *  1/1998

OTHER PUBLICATIONS

Chen et al, Development of natural crude drug resources from Taiwan, in vitro studies of the inhibitory effect on 12 microorganisms, The Japanese journal of pharmacognosy, 1987; 41 (3): 215-225.*
Nomura et al, Components of root bark of Morus australis, Planta medica, 1983; 49 (2): 90-94.*
Shi et al, Phenolic constituents of the root bark of Chinese Morus australis, Natural medicine 55 (3), 143-146, 2001.*
Fukai et al, Structure of Sanggenon G, a new diels-alder adduct from the Chinese crude drug "sang bai-pi" (morus root bark), Meterocycles, 30 (4): 611-615.*
Shi et al, Phenolic cnstituents of the root bark of Chinese Morus australis, Natural Medicine 55 (3), 143-146, 2001.*
Park et al, Kuwanon G: an antibacterial agent from the root bark of Morus alba against oral pathogens, Journal of Ethnopharmacology 84 (2003) 181-185.*

* cited by examiner

*Primary Examiner* — Qiuwen Mi
(74) *Attorney, Agent, or Firm* — Occhiuti Rohlicek & Tsao LLP

(57) ABSTRACT

An extract prepared from the root barks of *Morus australis* Poir. and its use as an anti-bacteria agent, and use of a compound Kuwanon H having the following formula (I) separated from the extract as an anti-bacteria agent:

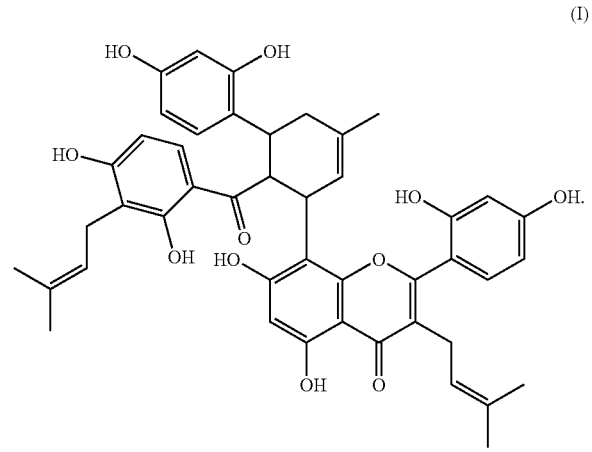

4 Claims, No Drawings

ANTI-BACTERIAL USE OF EXTRACT FROM *MORUS AUSTRALIS* POIR. AND COMPOUND KUWANON H

FIELD OF THE INVENTION

The present invention is related to use of an extract prepared from the root barks of *Morus australis* Poir. and a compound Kuwanon H separated from the extract in treating a bacteria infection.

BACKGROUND OF THE INVENTION

JP10-007555 discloses five compounds separated from an extract of tree bark of a mulberry tree such as *Morus bombycis* Koidz, *Morus alba* L., and *Morus Lhou* Koidz, which are mulberrofuran C, D, and G, kuwanol A and sanggenone G, and the anti-bacterial use of the five compounds against such as *Staphylococcus aureus* and Methicillin resistant *Staphylococcus aureus* (MRSA).

JP56-123979 discloses two compounds, kuwanon G and H, and their use in reducing the blood pressure of a hypertensive patient, which are separated from an extract prepared from root bark of a mulberry tree such as *Morus bombycis* Koidz, *Morus alba* L., and *Morus Lhou* Koidz.

SUMMARY OF THE INVENTION

An objective of the present invention is to provide an anti-bacterial use of Kuwanon H, a compound having the following formula (I):

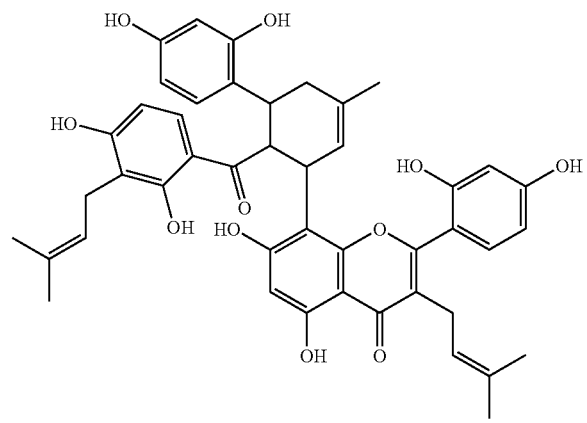

(I)

or a pharmaceutically acceptable salt thereof.

The above-mentioned anti-bacterial use of the present invention includes a pharmaceutical composition for treating a bacterial infection comprising, as a potent component, Kuwanon H, or a pharmaceutically acceptable salt thereof; use of Kuwanon H, or a pharmaceutically acceptable salt thereof in the manufacture of a medicament for treatment of bacterial infection in a patient; and a method of treating a subject having a bacterial infection, which comprises administering to said subject a therapeutically effective amount of kuwanon H, or a pharmaceutically acceptable salt thereof.

Another objective of the present invention is to provide an anti-bacterial use of an extract prepared from root bark of *Morus australis* Poir.

The anti-bacterial use of the extract according to the present invention includes a pharmaceutical composition for treating a bacterial infection comprising, as a potent component, the extract of the present invention; use of the extract of the present invention in the manufacture of a medicament for treatment of bacterial infection in a subject; and a method of treating a subject having a bacterial infection, which comprises administering to said subject a therapeutically effective amount of the extract of the present invention.

The "treating a bacterial infection" in the present invention extensively means treating any disorder caused by bacterial infection, or strictly means inhibiting growth of bacteria.

DETAILED DESCRIPTION OF THE INVENTION

"Sang-Bai-Pi" is a traditional Chinese herb, a dried root bark of *Morus alba* L., for anti-inflammation, releasing coughing and diuresis. The plant of *Morus alba* L. is rare in Taiwan; however, *Morus australis* Poir. can be easily found. These motivate the inventors of the present invention to prepare extracts from *Morus australis* Poir. and isolate compounds from the extract with industrially useful potential.

The present invention provides a method of treating a subject having a bacterial infection, which comprises administering to said subject a therapeutically effective amount of a compound having formula (I):

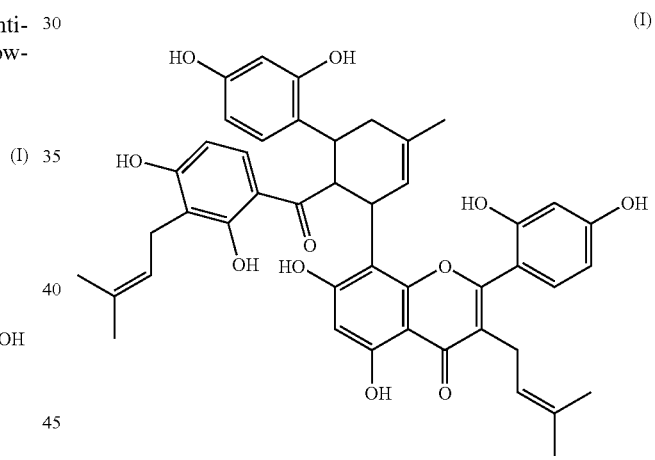

(I)

or a pharmaceutically acceptable salt thereof.

The present invention provides a method of treating a subject having a bacterial infection, which comprises administering to said subject a therapeutically effective amount of an extract prepared from root bark of *Morus australis* Poir., wherein the extract is prepared by a process comprising the following steps:

a) extracting root bark of *Morus australis* Poir. with a polar solvent;

b) concentrating the resulting extract solution from step a);

c) introducing the resulting concentrate from step b) to a reverse phase chromatography column, and eluting the column with a first eluent and a second eluent in sequence, said first eluent having a polarity of about 50 wt % of ethanol aqueous solution and said second eluent having a polarity of about 95 wt % of ethanol aqueous solution; and d) collecting a second eluate from the elution of the column with the second eluent, and removing the second eluent from the second eluate by evaporation.

Preferably, the bacteria are Gram-positive bacteria.

Preferably, the bacteria are *Staphylococcus aureus* (Smith) or *Streptococcus pneumoniae*. More preferably, the bacteria are *Staphylococcus aureus* (Smith). Most preferably, the bacteria are *Staphylococcus aureus*, Methicillin Resistant (MRSA). More preferably, the bacteria are *Streptococcus pneumoniae*. Most preferably, the bacteria are *Streptococcus pneumoniae*, Erythromycin and Ampicillin Resistant.

Preferably, the extract of the present invention comprises the compound of the formula (I) and a compound, Sanggenon G, having the following formula (II):

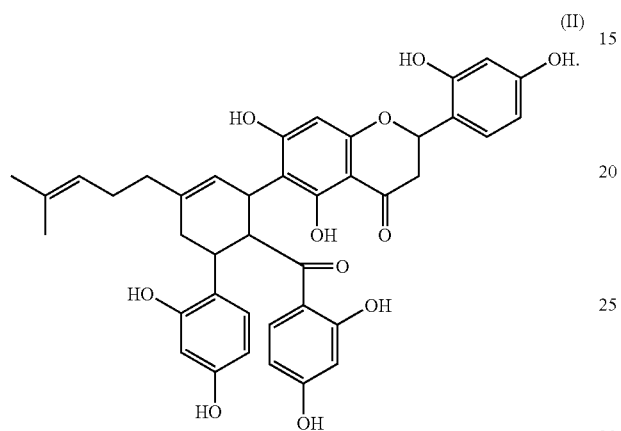

Preferably, the extract comprises 1-5% of the compound (I) and 1-5% of the compound (II), based on the weight of the extract. More preferably, the extract comprises about 3.7% of the compound (I) and 2.3% of the compound (II), based on the weight of the extract Preferably, the first eluent is a 50 wt % ethanol aqueous solution and the second eluent is a 95 wt % ethanol aqueous solution.

Preferably, the polar solvent in step a) is water or 95 wt % ethanol aqueous solution, wherein 95 wt % ethanol aqueous solution is more preferable.

The present invention will be better understood through the following examples which are merely illustrative, not for limiting the scope of the present invention.

Percentages and other amounts referred to in this specification are by weight unless indicated otherwise. Percentages are selected from any ranges used to total 100%.

EXAMPLE 1

Preparation of an Extract, EX-1

Sliced dried root barks of *Morus australis* Poir. (Moraceae) were pulverized and screen with a sieve. 100 g of the resulting powder was mixed with 95 wt % ethanol aqueous solution 1000 ml (10:1 (v/w)) in a round-bottom flask, and the resulting mixture was boiled under refluxing for one hour and filtered with a sieve of mesh number 350 and #2 filter paper to obtain a filtrate and a residue. The residue was subjected to the extraction under refluxing and the filtration under the conditions same as the above. The resulting two filtrates were combined, and a small portion thereof was dried by evaporation to calculate a dry power weight of the combined filtrate, which is 10.21 g, i.e. 10.21 wt % yield of crude extract. The combined filtrate was concentrated to 1/10 of its original weight, and to the resulting concentrate an equal weight of water was added. The resulting mixture was introduced to a reverse phase chromatography column packed with polystyrene adsorption resin (Diaion® HP20, Mitsubishi, Japan) in an amount of 30 times by dry weight of the concentrate of the combined filtrate, which was then eluted with 2 bed volumes (bed volume=600 ml) of 50 wt % ethanol aqueous solution (1200 ml), and then 2 bed volumes of 95 wt % ethanol aqueous solution (1200 ml) in sequence. The eluate from 95 wt % ethanol aqueous solution was collected and concentrated in vacuo to dry. 2.73 g of dry extract with a code name of EX-1 was thus obtained with a yield of 26.7%, based on the dry weight of the concentrate of the combined filtrate, and 2.73%, based on the weight of the dried root barks.

EXAMPLE 2

Separation of Extract EX-1

To a homogenous solution of 2 g EX-1 in 10 ml methanol 10 ml pure water was added, and the resulting mixture was then vigorously shaken to facilitate precipitating therein, followed by centrifugation at 10000 rpm for 15 minutes. The solid resulting from the centrifugation was subjected to the dissolution, precipitating and centrifugation steps. Total six cycles were carried out.

The six liquids obtained from the six centrifugations were combined and was concentrated in vacuo to dry (weight 1.3 g). The resulting dry powder was introduced to a silica gel column (3.2 cm×48.5 cm) packed with Silica Gel 60 in an amount of 30 times by weight of the dry powder, which was then eluted with 15 bed volumes (bed volume=250) of a mixed mobile phase of toluene:ethyl acetate=7:3 (3750 ml). The eluate was collected in a pre-determined number of bottles in sequence. The liquid in each bottle was concentrated in vacuo to dry, and a small amount of methanol was added back to dissolve the resulting dry powder, which was then introduced into a dextran gel column (1.5 cm×40 cm) packed with Sephadex LH-20 resin in an amount of 100 times by weight of the dry powder. The column was eluted with one bed volume of methanol (30 ml), and fractions of compounds P2-1, P2-2, P3-1 and P3-2 were obtained. Each fraction was concentrated in vacuo to dry, and then subjected to purification with preparative HPLC. Compounds P2-1, P2-2, P3-1 and P3-2 were obtained. Yield of compound P3-1 is 2.3% (46 mg), based on the weight of EX-1, and yield of compound P3-2 is 3.65% (73 mg), based on the weight of EX-1.

The residue after the six centrifugation was dissolved in methanol and the resulting solution was concentrated in vacuo to dry. The resulting dry powder was introduced to a silica gel column (3.2 cm×48.5 cm) packed with Silica Gel 60 in an amount of 30 times by weight of the dry powder, which was then eluted with two bed volumes (bed volume=250) of a mixed mobile phase of toluene:ethyl acetate=9:1 (500 ml). The eluate was collected in a pre-determined number of bottles in sequence. The liquid in each bottle was concentrated in vacuo to dry, and a small amount of methanol was added back to dissolve the resulting dry powder, which was then introduced into a dextran gel column (1.5 cm×40 cm) packed with Sephadex LH-20 resin in an amount of 100 times by weight of the dry powder. The column was eluted with one bed volume of methanol (30 ml), and compounds P3-3 and P3-4 were obtained.

Structure Analysis of Compounds P2-1, P2-2, P3-1, P3-2, P3-3 and P3-4

P2-1 Mulberrofuran C
$C_{34}H_{28}O_9$ MW = 580.59
2-[2,6-dihydroxy-4-(6-hydroxy-benzofuran-2-yl)-phenyl]-6-(2,4-dihydroxy phenyl)-4-methyl-cyclohex-3-enyl]-(2,4-dihydroxy-phenyl)-methanone

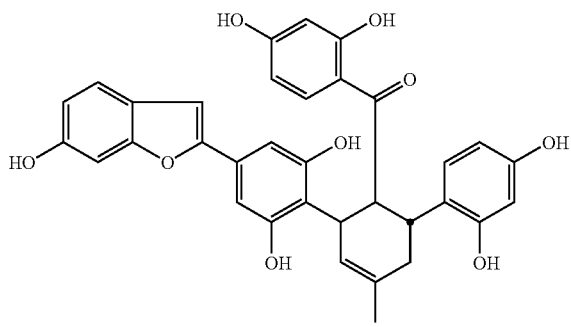

P2-2 Kuwanon G (Albanin F)
$C_{40}H_{36}O_{11}$ MW = 692.72
[6-(2,4-dihydroxy-benzoyl)-5-(2,4-dihydroxy-phenyl)-3-methyl-cyclohex-2-enyl]-2-(2,4-dihydroxy-phenyl)-5,7-dihydroxy-3-(3-methyl-but-2-enyl)-chromen-4-one

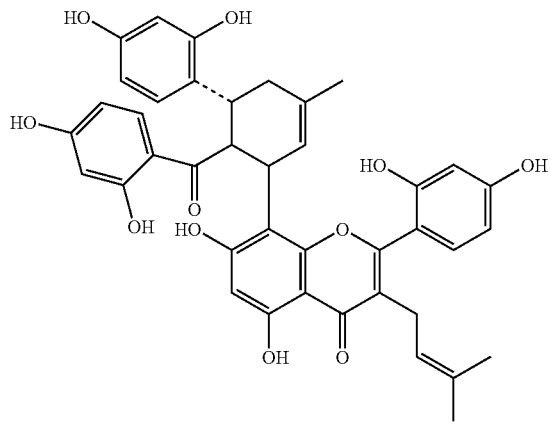

P3-1 Sanggenon G
$C_{40}H_{38}O_{11}$ MW = 694.74
[6-(2,4-dihydroxy-benzoyl)-5-(2,4-dihydroxy-phenyl)-3-(4-methyl-pent-3-enyl)-cyclohex-2-enyl]-2-(2,4-dihydroxy-phenyl)-5,7-dihydroxy-chroman-4-one

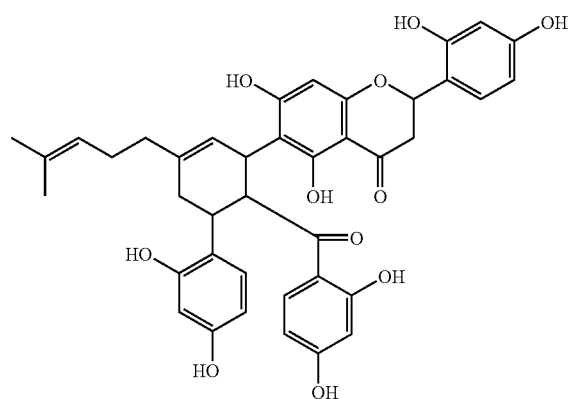

P3-2 Kuwanon H (Albanin A)
$C_{45}H_{44}O_{11}$ MW = 760.84
8-[6-[2,4-dihydroxy-3-(3-methyl-but-2-enyl)-benzoyl]-5-(2,4-dihydroxy-phenyl)-3-methyl-cyclohex-2-enyl]-2-(2,4-dihydroxy-phenyl)-5,7-dihydroxy-3-(3-methyl-but-2-enyl)-chromen-4-one

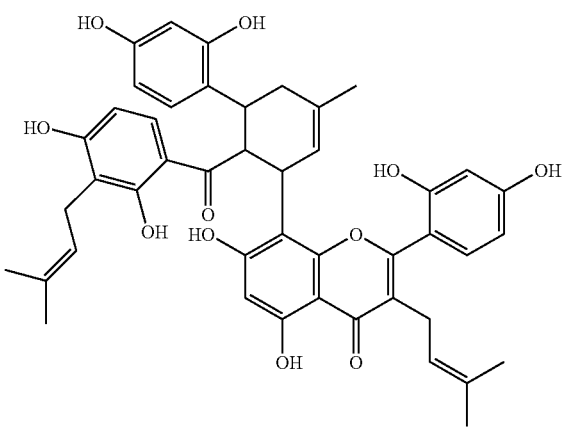

P3-3 Morusin
$C_{25}H_{24}O_6$ MW = 420.46
2-(2,4-dihydroxy-phenyl)-5-hydroxy-8,8-dimethyl-3-(3-methyl-but-2-enyl)-8H-pyrano[2,3-f]chromen-4-one

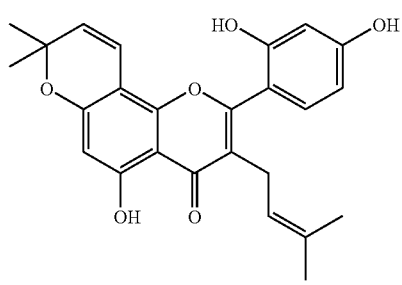

P3-4 Mulberrofuran D
$C_{29}H_{34}O_4$ MW = 446.59
3,7-dimethyl-octa-2,6-dienyl)-6-hydroxy-benzofuran-2-yl]-4-(3-methyl-but-2-enyl)-benzene-1,3-diol

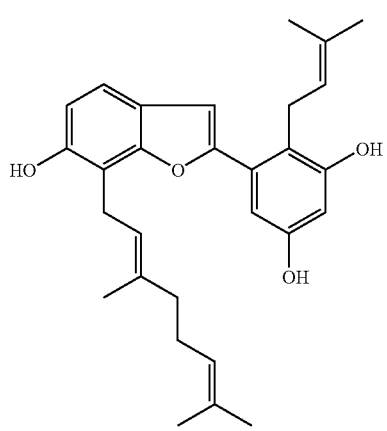

P2-1: ESI-MS: m/z 603.3 ([M+Na]$^+$) and m/z 579.2 ([M−H]$^-$). The NMR analysis were also carried out. The ESI-MS and NMR data indicate the formula of P2-1 is $C_{34}H_{28}O_9$. The NMR data were compared with the study of Fukai, T.; Hano, Y.; Hirakura, K.; Nomura, T.; Uzawa, J.; Fukushima, K., *Structure of mulberrofuran J, a 2-arylbenzofuran derivative from the cultivated mulberry tree (Morus lhou Koidz.)*, Heterocycles 1984, 22, 1007-1011, and compound P2-1 is confirmed to be mulberrofuran C reported in said study. Mulberrofuran C is also disclosed in Japanese patent publication JP57-144223.

P2-2: ESI-MS: m/z 715.3 ([M+Na]$^+$) and m/z 691.3 ([M–H]$^-$). The NMR analysis were also carried out. The ESI-MS and NMR data indicate the formula of P2-2 $C_{40}H_{36}O_{11}$. The NMR data were compared with the study of Nomura, T.; Fukai, T.; Narita, T., *Hypotensive constituent, kuwanon H, a new flavone derivative from the root bark of the cultivated mulberry tree (Morus alba L.)*, Heterocycles 1980, 14, 1943-1951, and compound P2-2 is confirmed to be albanin F (Kuwanon G) reported in said article. Albanin F (Kuwanon G) is also disclosed in Korean patent publication KR20020087225.

P3-1: ESI-MS: m/z 695.4 ([M+H]$^+$) and m/z 693.7 ([M–H]$^-$). The NMR analysis were also carried out. The ESI-MS and NMR data indicate the formula of P3-1 is $C_{40}H_{38}O_{11}$. The NMR data were compared with the study of Fukai, T.; Hano, Y.; Fujimoto, T.; Nomura, T., *Structure of sanggenon G, a new Diels-Alder adduct from the Chinese crude drug "Sang-Bai-Pi" (Morus root barks)*, Heterocycles 1983, 20, 611-615, and compound P3-1 is confirmed to be Sanggenon G Sanggenon G is also disclosed in Japanese patent publication JP10-007555.

P3-2: ESI-MS: m/z 761 ([M+H]$^+$), 783 ([M+Na]$^+$) and 759 ([M–H]$^-$). The molecular weight of P3-2 was calculated as 760. The NMR analysis were also carried out. The ESI-MS and NMR data indicate the formula of P3-2 is $C_{45}H_{44}O_{11}$. The NMR data were compared with the studies of Nomura, T.; Fukai, T.; Narita, T.; Terada, S.; Uzawa, J.; Iitaka, Y.; Takasugi, M.; Ishikawa, S. I.; Nagao, S.; Masamune, T., *Confirmation of the structures of kuwanons G and H (albanins F and G) by partial synthesis*, Tetrahedron Letters 1981, 22, 2195-2198; Oshima, Y.; Konno, C.; Hikino, H., *Structure of moracenin A, a hypotensive principle of Morus root barks*, Heterocycles 1980, 14, 1287-1290; and Oshima, Y.; Konno, C.; Hikino, H.; Matsushita, K., *Structure of moracenin B, a hypotensive principle of Morus root barks*, Tetrahedron Letters 1980, 21, 3381-3384, and compound P3-2 is confirmed to be Kuwanon H (also called Albanin A or Moracenin A. Japanese patent publication JP56-123979 discloses Kuwanon H is potent in reducing the blood pressure of a hypertensive patient.

P3-3: ESI-MS: m/z 421 ([M+H]$^+$). The NMR analysis were also carried out. The ESI-MS and NMR data indicate the formula of P3-3 is $C_{25}H_{24}O_6$. The NMR data were compared with the study of Nomura, T.; Fukai, T.; Yamada, S.; Katayanagi, M., *Phenolic constituents of the cultivated mulberry tree (Morus alba L.)*, Chem. Pharm. Bull. 1976, 24, 2898-2900, and compound P3-3 is confirmed to Morusin. Morusin is also disclosed in US patent publication US2008/0286213.

P3-4: ESI-MS: m/z 447.0 ([M+]$^+$). The NMR analysis were also carried out. The ESI-MS and NMR data indicate the formula of P3-4 is $C_{29}H_{34}O_4$. The NMR data were compared with the study of Nomura, T.; Fukai, T.; Shimada, T.; Chen, I.-S. Mulberrofuran D, *a new 2-arylbenzofuran from the root barks of the mulberry tree (Morus australis Poir.)*, Heterocycles, 1982, 19, 1855-1860, and compound P3-4 is confirmed to be Mulberrofuran D. Mulberrofuran D is also disclosed in Japanese patent publication JP10-007555.

Anti-Microbial Test

*Staphylococcus aureus* (Smith), and *Staphylococcus aureus*, Methicillin Resistant (ATCC 33591), In Vitro Bacteria Minimum inhibitory concentration (MIC) of sample on *Staphylococcus aureus* (Smith) and *Staphylococcus aureus*, Methicillin Resistant (ATCC 33591) was determined by the broth dilution method [Edwards J. R. et al. In vitro antibacterial activity of SM-7338, a carbapenem antibiotic with stability to dehydropeptidase I. Antimicrobial Agents Chemotherapy. 33: pp. 215-222, 1989]. The test substance was dissolved (generally 100% DMSO) and serially diluted in solvent to desired stock concentrations. For each concentration tested, a 0.01 ml aliquot (1% DMSO final concentration) was added to a 48-well plate after which 0.99 ml of Mueller-Hinton Broth (DIFCO, USA.) with 1-5×10$^5$ CFU/ml of *Staphylococcus aureus* (Smith) or *Staphylococcus aureus*, Methicillin Resistant (ATCC 33591) was added. Thus, final maximal concentration of DMSO was 1% and the initial test substance concentration was 100 μg/ml or 30 μM. The plates were incubated at 37° C. for 20 hours and then visually examined and scored positive (+) for inhibition of growth or turbidity or negative (–) for no effect upon growth or turbidity. Vehicle-control and active reference agents were used as blank and positive controls, respectively. Each concentration was evaluated in duplicate. The results are shown in Table 1. *Streptococcus pneumoniae* (ATCC 6301) and *Streptococcus pneumoniae* (Erythromycin and Ampicillin Res. Clin. Isol.), In Vitro Bacteria Minimum inhibitory concentration (MIC) of sample on *Streptococcus pneumoniae* and *Streptococcus pneumoniae* (Erythromycin and Ampicillin Res. Clin. Isol.) was determined by the broth dilution method [Edwards J. R. et al. In vitro antibacterial activity of SM-7338, a carbapenem antibiotic with stability to dehydropeptidase I. Antimicrobial Agents Chemotherapy. 33: pp. 215-222, 1989.]. The test substance was dissolved (generally 100% DMSO) and serially diluted in solvent to desired stock concentrations. For each concentration tested, a 0.01 ml aliquot (1% DMSO final concentration) was added to a 48-well plate after which 0.99 ml of Tryptic Soy Broth (DIFCO, U.S.A.) containing 7% fetal bovine serum with 1-5×10$^5$ CFU/ml of *Streptococcus pneumoniae* (ATCC 6301) or *Streptococcus pneumoniae* (Erythromycin and Ampicillin Res. Clin. Isol.) was added. Thus, final maximal concentration of DMSO was 1% and the initial test substance concentration was 100 μg/ml or 30 μM. The plates were incubated at 37° C. for 20 hours and then visually examined and scored positive (+) for inhibition of growth or turbidity or negative (–) for no effect upon growth or turbidity. Vehicle-control and active reference agents were used as blank and positive controls, respectively. Each concentration was evaluated in duplicate. The results are shown in Table 1.

TABLE 1

Minimum inhibitory concentration (MIC) of Extract EX-1 and single compound in anti-microbial test

| Sample | MIC (μg/ml) | | | |
|---|---|---|---|---|
| | SA (Smith) | MRSA | SP | SP (EM & AM Res.) |
| EX-1 | 0.3 | 1 | 30 | 30 |
| P2-1 | 3 | >100 | 100 | 30 |
| P2-2 | 3 | >100 | 30 | 30 |
| P3-1 | 1 | 3 | 30 | 10 |
| P3-2 | 0.3 | 0.3 | 10 | 10 |
| P3-3 | 10 | 100 | 100 | 30 |
| P3-4 | 3 | 100 | 30 | 10 |
| Gentamicin | 0.1 | 1 | 100 | 100 |
| Ampicillin | 0.1 | 30 | 0.01 | 3 |

SA (Smith): *Staphylococcus aureus* (Smith);
MRSA: *Staphylococcus aureus*, Methicillin Resistant;
SP: *Streptococcus pneumoniae*;
SP (EM & AM Res.): *Streptococcus pneumoniae*, Erythromycin and Ampicillin resistant, clinical isolates.

It can be seen from Table 1 that compound P3-2 is very potent in inhibiting growth of SA (smith) and MRSA with MIC of both 0.3 µg/ml. In contrast, MIC of Gentamicin on MRSA is 10 times to that on SA (Smith).

Compound P3-1 shows potency in inhibiting growth on SA (Smith) and MRSA with MIC of 1 and 3 µg/ml, respectively. Compound P3-1 is relatively less potent in inhibiting growth on SP and SP (EM & AM Res.) with MIC of 30 and 10 µg/ml, respectively.

Surprisingly, the Extract EX-1 of the present invention shows very strong inhibition on growth of SA and MRSA with MIC of 0.3 and 1 µg/ml, respectively, in view of the contents of P3-2 and P3-1 being respectively 3.65 wt % and 2.3 wt % therein. It is apparent that components contained in the extract EX-1 create a synergistic effect on inhibiting the growth of SA and MRSA, so that the extract EX-1 has very low MIC values on SA and MRSA.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

The invention claimed is:

1. A method of treating a subject having a bacterial infection, which comprises administering to said subject a therapeutically effective amount of an isolated compound having formula (I):

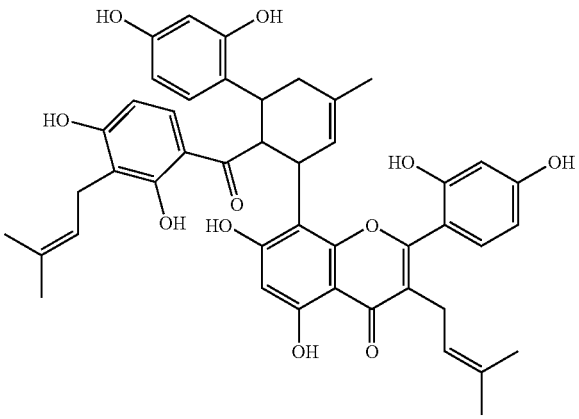

(I)

or a pharmaceutically acceptable salt thereof.

2. The method of claim 1, wherein the bacterial infection is caused by Gram-positive bacteria.

3. The method of claim 1, wherein the bacterial infection is caused by *Staphylococcus aureus* (Smith) or *Streptococcus pneumoniae*.

4. The method of claim 1, wherein the bacterial infection is caused by Methicillin Resistant *Staphylococcus aureus* or Erythromycin and Ampicillin Resistant *Streptococcus pneumoniae*.

* * * * *